United States Patent [19]

Dehe et al.

[11] Patent Number: 5,195,364

[45] Date of Patent: Mar. 23, 1993

[54] METHOD AND APPARATUS FOR TESTING THE HARDNESS OF A WORKPIECE BY THE PENETRATION METHOD

[75] Inventors: Hans-Jürgen Dehe, Essen; Heinz Bösebeck, Mettmann; Wolfgang Ruyters, Ratingen, all of Fed. Rep. of Germany

[73] Assignee: Mannesmann Aktiengesellschaft, Dusseldorf, Fed. Rep. of Germany

[21] Appl. No.: 713,872

[22] Filed: Jun. 12, 1991

[30] Foreign Application Priority Data

Jun. 12, 1990 [DE] Fed. Rep. of Germany ....... 4019120
Jun. 11, 1991 [DE] Fed. Rep. of Germany ....... 4119564

[51] Int. Cl.$^5$ ............................................. G01N 3/42
[52] U.S. Cl. ........................................ 73/81; 73/82
[58] Field of Search ............................... 73/81, 82, 83

[56] References Cited

U.S. PATENT DOCUMENTS

| | | | |
|---|---|---|---|
| 3,295,363 | 1/1967 | Delporte | 73/81 |
| 3,822,946 | 7/1974 | Rynkowski | 73/81 |
| 4,635,471 | 1/1987 | Rogers et al. | 73/81 |
| 4,719,793 | 1/1988 | Pozo | 73/81 |
| 4,852,397 | 8/1989 | Haggag | 73/82 |

OTHER PUBLICATIONS

Abstract of Japanese Patent JP 60-143739.

*Primary Examiner*—Hezron E. Williams
*Assistant Examiner*—Howard Wisnia
*Attorney, Agent, or Firm*—Cohen, Pontani, Lieberman, Pavane

[57] ABSTRACT

A method of testing the hardness of a workpiece having a continuously curved outer surface, in particular a pipe or rod, by the penetration method, includes (a) holding the workpiece in a horizontally and vertically fixed position; (b) arranging a machine tool and a hardness testing instrument having a penetration body above the workpiece for movement with respect to the workpiece; (c) linearly scanning a predetermined area of the curved surface of the workpiece for determining the distance between a distance sensor and the curved surface, the region lying in the horizontal path of the machine tool; (d) determining the summit point of the scanned curved surface area from the scanning operation of step (c); (e) selecting the scanned curved area as the test location for the horizontal positioning of the hardness testing instrument; (f) selecting a locus along the scanned curved area of the workpiece as the reference point for the vertical positioning of the machining tool; (g) machining a region into the surface of the workpiece; (f) pressing the penetration body with a defined force into the machined region to generate an impression surface into the machined region of the workpiece; and (i) determining the hardness of the workpiece from the surface of the depression. An apparatus for performing the method is also disclosed.

4 Claims, 5 Drawing Sheets

METHOD AND APPARATUS FOR TESTING THE HARDNESS OF A WORKPIECE BY THE PENETRATION METHOD

FIELD OF THE INVENTION

The present invention relates to a method and an apparatus for testing the hardness of a workpiece, especially pipes or rods, whereby a workpiece having a continuously curved surface is automatically scanned, machined, and the hardness values determined.

BACKGROUND OF THE INVENTION

The present invention relates to a method and an apparatus for testing through known penetration methods the hardness of a workpiece having a continuously curved outer surface, such as pipes or rods.

Depending on the use, a workpiece made of for example steel, and manufactured by various methods, must in many cases meet minimum toughness standards. Compliance with these standards can be ascertained by chemical analysis, observation of the nature and amount of deformation, with subsequent optional heat treatment, or a combination thereof. In this regard, the heat treatment may be an integral part of the method of manufacture or constitute a separate step within a sequence of different operating steps. In order to be able to test for compliance with the required minimum hardness not only during the course of the final acceptance testing, but during other relevant phases, the result of the heat treatment should be checked in accordance with the principles of controlled manufacture by a hardness test which is carried out on each piece or in accordance with a random sampling plan.

By means of known reference tables, the hardness value found can then be associated with a corresponding hardness or tensile strength value. Since hardness measurements should be taken, when possible, during the course of manufacture, a test station having a hardness testing instrument is arranged behind the heat-treatment unit. Depending on the cooling conditions, the test station can be located either immediately behind the heat-treatment unit or somewhat further removed therefrom. The test station consists essentially of a holding device which fixes the workpiece in position, a device which bears the working tool, and a hardens testing instrument. The Brinell method or the Vickers method is used, with perference being given in most cases to the Brinell method. The test method is carried out in such a manner that, after the workpiece has been fixed in position on the roller table, a point on the surface of the workpiece which lies within the test region is machined in order to produce a flat and smooth test surface. The machining of the test surface is done by milling or grinding with a predetermined depth. The pressing of the penetration body into the test region, through the use of a ball or a pyramid, is done with a defined force, and in the ideal case, precisely within the central region of the machined surface. The imprint of the resultant impression area is transferred in a known manner by means of a swingable optical system onto a screen. The examining person can then determine the size of the penetration surface with the aid of known means by measurement of its diameter or diagonal. This area then constitutes, with respect to comparative values of reference pieces, a measure of the hardness of the workpiece tested. In order to carry out this known method substantially automatically, it has already been proposed that a test laboratory, by a contact-free manner, scan the surface impression produced by the ball on the surface of the workpiece by means of a camera (see in this connection the prospectus of Foundrax Engineering Products Limited). The camera is connected to an evaluation unit which, by means of known mathematical algorithms, converts the measured value into the corresponding hardness value.

From Federal Republic of Germany 39 01 432 it is furthermore known that a determination of the ball indentation diameter can be made with sufficient accuracy on a Brinell hardness testing machine, by means of a video camera, a digitizer and a computer, as well as suitable software.

One testing device of this type which is suitable for the testing of the hardness of pipes or rods is known from U.S. Pat. No. 4,635,471. A vertically moveable mount having a V-block for the workpiece as well as a horizontally and vertically displaceable device, on which a machining tool and a hardness testing instrument are fastened, are arranged on a rack. The workpiece is fixed in position on the V-block by clamping holders which are displaceable in guide rails and the displaceable arrangement is then positioned on the axis of the pipe. This testing device has the disadvantage that a lateral and/or vertical offset of the testing place with respect to the axis of the V-surface resulting from a curved and/or oval pipe cannot be automatically compensated for and machining, for instance milling, may in the extreme case be effected too deep or not at all and, therefore, the predictive power of the values obtained at different depths of material is limited.

JP 70-143739 A discloses an automatically operating hardness testing instrument in which the picture contour is recognized by a sensor which scans the test piece and a test locus, the coordinates of which have been previously established, is automatically found by comparison with a desired picture which is stored in a computer. For this purpose, the resting surface for the test piece is displaceable in x and y directions. By this method it is intended to provide assurance that the same point is always tested for a number of identical test pieces. Furthermore, with this method the hardness penetration can be placed in a region which does not limit the use of the workpiece.

SUMMARY OF THE INVENTION

It is an object of the present invention to provide a method and an apparatus for testing the hardness of a workpiece by which automatic hardness testing of high predictive value is made possible during production flow for workpieces having a continuously curved outer surface, such as pipes or rods.

These and other objects of the present invention are achieved by providing a method of testing the hardness of the workpiece having a continuously curved outer surface, in particular a pipe or rod, by the penetration method, comprising: (a) holding the workpiece in a horizontally and vertically fixed position; (b) arranging a machine tool and a hardness testing instrument having a penetration body above said workpiece for movement with respect to said workpiece; (c) linearly scanning a predetermined area of said curved surface of said workpiece for determining the distance between a distance sensor and said surface, said region lying in the horizontal path of said machine tool; (d) determining the summit point of said scanned curved surface area from said scanning operation of step (c); (e) selecting said scanned curved area as the test location for the horizontal positioning of said hardness testing instrument; (f) selecting a locus along said scanned area of said workpiece as the reference point for the vertical positioning of said machine tool; (g) machining a region into the surface of said workpiece; (h) pressing said penetration body with a defined force into said machined region to generate an impression surface in said machined region of said workpiece, and (i) determining the hardness of said workpiece by the surface size of said depression.

The apparatus in accordance with the present invention comprises a workpiece support having an axis; means for holding said workpiece in contact with said support; a machining tool and a hardness testing instrument; means for holding said machining tool and said hardness testing instrument, said holding means being vertically adjustable and horizontally movable for moving and positioning said machining tool and said hardening testing instrument along an arcuate path about an axis of rotation and over said workpiece, said axis of rotation being disposed at a predetermined distance from and perpendicular to said axis of said workpiece support; a first distance sensor disposed in front of said machining tool and movable along said arcuate path; and a control unit electrically connected to said first distance sensor.

In the preferred embodiment of the present invention it is essential that, by means of a distance sensor, the contour of the outer surface of the workpiece within the region of the movement of the machining tool is determined and a summit point or zenith is detected before machining the surface of the workpiece and that the horizontal positioning of the hardness testing instrument is oriented at the summit point of the contour.

The advantage of the present invention is that, by the determining the summit point of the continuously covered of the surface of the workpiece, the hardness testing instrument can be positioned precisely horizontally so that assurance is had that the penetration of the penetration body takes place in the central region of the machined area. The hardness values thereby ascertained are of a high predictive value and the range of variation of the measurement values is very small.

If the hardness testing were carried out in a test laboratory, there would normally be no difficulty in optimally adjusting the conditions necessary for the hardness measurement and thereby obtaining hardness values of predictive value. However, hardness, testing during the flow of a production line, on the other hard, encounters problems not apparent under laboratory conditions. One of the difficulties is in assuring a precise vertical positioning of the machining tool, for instance a grinding wheel or miller, on the summit point or zenith of the curved surface in order to obtain a well-defined depth of machining. In the ideal case of a linear pipe or rod of circular cross section, the line of the outer surface of the pipe lying in the summit point is precisely aligned with the machine axis of the testing device after the application of the clamping device. Only under these ideal conditions is it relatively easy to position the machining tool and the hardness testing instrument on the axis of the machine so as to obtain reproducible results by exact placement on the summit point. In practical reality, pipes, however, are frequently very slightly crooked and their cross section are not always circular. In such cases it is not out of the question that in the event of an oval pipe cross section the center point of the surface machined lies alongside the axis of the machine. Since the machine tool is customarily set to the nominal outside diameter of the pipe or rod and thus to a fixed vertical position, either no machining takes place or, in the other extreme event, machining is effected to a depth which impairs the wall thickness, with the danger that the curved surface of the workpiece will be notched impermissibly deep. Upon a positioning with a small desired depth value, the desired depth of machining is in most cases not obtained. If then, in accordance with the known method, the hardness testing instrument is adjusted to the axis of the machine it is then possible that the hardness impression in workpieces of steel still lies within the region of the decarburization zone and thus the toughness indicated is actually too low.

All the above-mentioned difficulties are eliminated by the method of the invention since, by the scanning of the contour of the surface of the workpiece, the summit point thereof can always be ascertained and the machining tool can be positioned properly vertically and the hardness testing instrument horizontally. The method proposed is of particular advantage for long, heavy pipes, for instance, 12 meters long and a weight of more than one ton, in which case it is not possible to bring the axis of the pipe into agreement by a clamping force with the axis of the machine of the test station. This means that it is sufficient for the pipe or the rod to be held in position by a holding-down device, regardless of the position which the pipe axis assumes with respect to the axis of the machine.

For example, in one practical case, deviations of the position of the summit point or zenith from the axis of the machine of ±50 mm still lie within the positioning region of the machining tool and the hardness testing instrument. In addition to the lateral offset, the vertical offset is also taken into account by the possibility of adjustment of the depth of machining. For this purpose, the lower edge of the holding-down device is detected and the contact with the surface of the workpiece is selected as reference point for the vertical positioning of the machining tool. With reference to this point, the machining depth of the tool is then preestablished, for instance at a value of −0.3 mm with a position range of −5 mm.

The selection of the contact of the holding-down device with the surface of the workpiece as reference point for the vertical positioning of the machining tool is sufficient for workpieces with substantially flat surface and, for example, for rods in which the position of the depth of the hardness impression plays a minor role. The method becomes more precise if the previously determined summit point or zenith of the curved workpiece surface is selected as reference point. With this method, assurance is had that even in the case of an undulated or uneven surface of the workpiece, a machined surface with precisely defined depth position is reproducibly produced regardless of the vertical position of the holding-down device. For use in practice there can be employed the distance sensor which scans the curved contour, in which connection it should have a measurement precision within the 1/100 mm range. It is easier from a control standpoint to provide a second distance sensor which is coupled with the machining tool and which is positioned on the previously ascertained summit point. This second distance sensor operates, for instance, in accordance with the principle of laser technology and has a precision of measurement of ±100 mm so that the machining tool can be set to a precision with respect to depth of ±1/10 mm. The first distance sensor which scans the contour can, in contradistinction to this, effect a very rough measurement since a tolerance of ±1 mm is sufficient for the horizontal detection of the summit point. When two distance sensors are used, the adjustment of the depth is effected in the manner that the rough setting for the depth of machining is effected by the vertical position of the holding-down device and, after measurement of the distance from the summit point by means of the second distance sensor, the fine adjustment is effected for the machining tool.

For carrying out the above method, it is proposed that a test station which, in known manner, consists of a workpiece holder, a device which holds the machining tool, a hardness testing instrument and an evaluation system which is electrically connected to a scanning device. To these devices which are already known that is added in accordance with the invention a distance sensor which, together with the machining tool and the hardness testing instrument, is fastened in the sequence indicated on a swinging device, the axis of rotation of which is arranged at a defined distance from the machine axis of the test station. By means of this swinging device the aforementioned devices can be swung into the test region and positioned. The test method now proceeds in the manner that the sensor scanning the contour of the curved surface of the workpiece is swung in a horizontal arc over the region of the workpiece to be tested and, after detection of the workpiece edges, the distance from the fixed point of the sensor to the surface of the workpiece is continuously measured. The measurement values are fed to a control instrument which, from the parabolic course of the contour line, calculates the position of the center of the summit and, by means of known mathematical algorithms, determines the angle of above mentioned swing of the swinging device which corresponds to this point. The hardness testing instrument which is arranged on the swinging device behind the distance sensor and the machining tool and which, like the distance sensor and the machining tool, lies on the same diameter of swing is positioned precisely on the summit point of the contour line corresponding to the angle of swing determined. In this way, the result is obtained that the hardness indentation takes place in the center of the machining surface. In order to further improve the above method, it is also proposed that the machining tool be arranged on a vertically adjustable device which is connected to the swinging device and that the precise vertical adjustment be oriented on the reference point of another distance sensor. The purpose of the improvement is that, referred to the summit point determined, any desired depth of machining with different vertical offset of the workpiece is constantly controlled. The previously known large deviations of the measured hardness values are thereby substantially reduced since the depth of machining can be adjusted corresponding to the empirical values via the expected depth of the edge decarburization, in the manner that the penetration body is always pressed into the non-decarburized region. As distance sensors there can be used all types available on the market, regardless of whether the scanning takes place mechanically, inductively, capacitively or optically, the signals being forwarded in analog or digital form to the control instrument. An inductively operating type has proven advantageous for the first distance sensor and a type based on laser technology for the second. The said first distance sensor can be obtained at low cost since the precision of measurement required from it is not very high. The second distance sensor is considerably more expensive but has the advantage that as a result of this arrangement of two sensors, control expense is saved as compared with the use of only one sensor.

The determination of the size of the impression or indentation surface is effected in known manner by optical scanning of the picture projected on a ground glass or screen. As a scanning instrument a diode-matrix camera is used which operates in accordance with the light-dark differentiation principle. The method of evaluation is similar to the known method and its object also is to compare the hardness value which can be calculated via the determination of the area with a predetermined desired value. As already mentioned, this comparison is also used to form a control signal in order to be able to sort the workpieces tested.

The test station of the invention can be further improved by also fastening to the swinging device a wall-thickness measuring instrument which operates without contact, for instance a U.S. testing unit. Since the U.S. test instrument can be positioned in the same manner as the machining tool and the hardness testing instrument, the wall thickness which corresponds in accordance with the secant applied, to the thinnest point of the surface machined is precisely measured. In this way, one prevent the delivery of pipes in which the minimum wall thickness to be maintained is not present due to the machined surface for the hardening test at the machined point.

BRIEF DESCRIPTION OF THE DRAWINGS

Preferred embodiments of the method of the invention and the corresponding apparatus will be explained in further detail and in reference to the drawings, in which.

DESCRIPTION OF THE PRESENTLY PREFERRED EMBODIMENTS

Figure 1A:
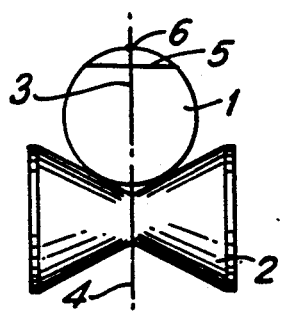
FIG. 1A shows diagrammatically the position of a pipe to be tested in the ideal state.
Figure 1C:
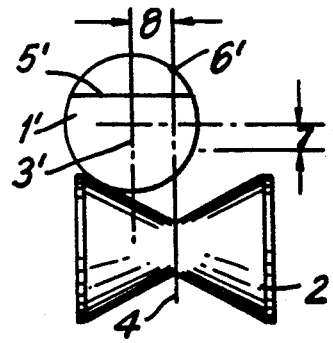
FIG. 1C shows diagrammatically the position of a tube with vertical and lateral offset which is to be tested.
Figure 1B:
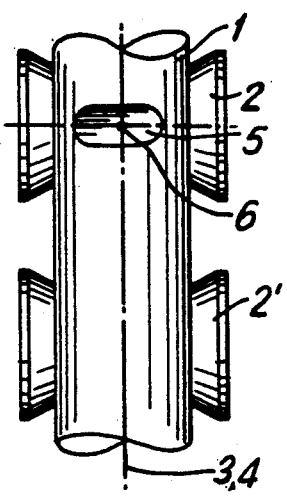
FIG. 1B is a top view of FIG. 1A.

FIGS. 1A and 1B show diagrammatically the position of a pipe 1 in ideal state which is to be tested. The pipe 1 lies on a roller 2 which is developed as a double cone and which is part of a roller table, not shown. In this quasi-laboratory state, the axis 3 of the pipe 1 is aligned with the machine axis of the testing device 4, so that a machining tool (not shown here) which is directed on this machine axis 4 produces a machined surface 5 (shown here greatly exaggerated) which is perpendicular to the axis 3 of the pipe 1 and the center of which is aligned with the summit point 6 of the pipe 1.

In the top view (1B) the contour of the machined surface 5 can be noted. This illustration is valid under the assumption that the displacement path of the machining tool is perpendicular to the machine axis 4.

Figure 1D:
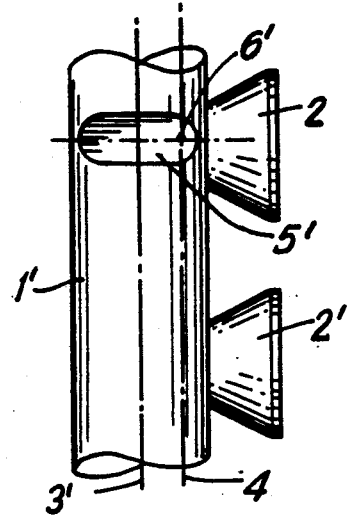
FIG. 1D is a top view of FIG. 1C.
Figure 1E:
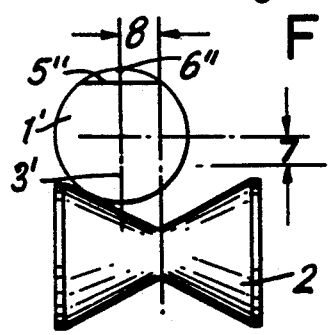
FIG. 1E shows diagrammatically the position of a pipe to be tested with vertical and lateral offset and summit point determined.
Figure 1F:
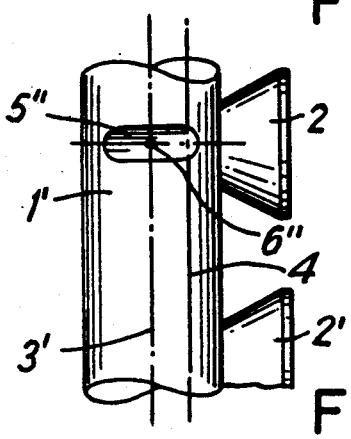
FIG. 1F is a top view of FIG. 1E.

As compared therewith, FIGS. 1C and 1D show diagrammatically the position of a pipe 1' with vertical offset 7 and lateral offset 8 which is to be tested. Assuming that the machining tool is still directed in height on the ideal position shown in FIGS. 1A and 1B, there is produced, shown greatly exaggerated, a machined area 5' which is completely unusable for the hardness testing since it would lead to the destruction of the pipe 1'. Furthermore, the point of testing 6' for the hardness indentation would no longer lie in the center of the machined area 5', but on the edge thereof. In accordance with FIGS. 1E and 1F, in order to overcome this problem, the contour of the curved pipe surface is determine din accordance with the invention by means of a sensor 9 (FIG. 3) and the summit point 6'' is determined from the measured values. The determined summit point or zenith 6'', which is at the same time the test location for the positioning of the penetration body 18 (FIG. 3) of the hardness testing instrument (not shown), is a prerequisite for the production of a usable machined area 5'' for a pipe 1' which is located with vertical and lateral offset 7, 8. The hardness indentation then takes place in the center of the machined area 5''.

Figure 2:
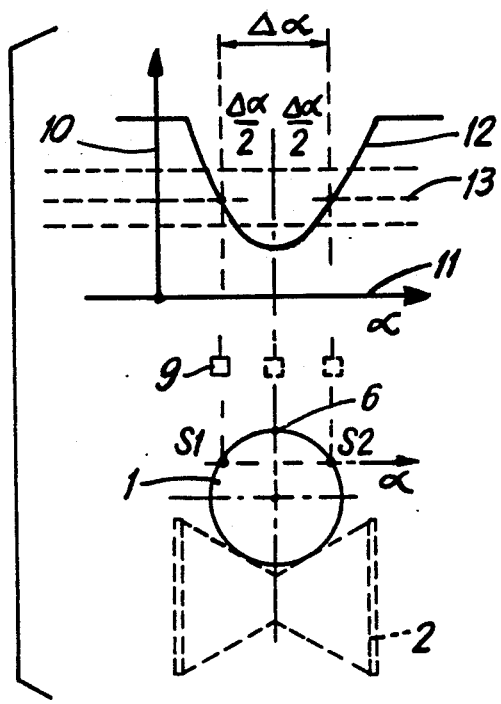
FIG. 2 shows diagrammatically the detection of the contour of the pipe to be tested.

The method of measurement for determining the summit point is shown diagrammatically in FIG. 2A. In the lower part of the FIG. 2A a pipe 1 to be tested is mounted on a roller 2 in a manner similar to that shown in FIG. 1A. In the upper part of the Fig. the received signal of the sensor 9 is plotted in a graph on the ordinate axis 10 while the path of travel alpha ($\alpha$) of the sensor 9 is plotted on the abscissa axis 11. Between these two parts of the FIG. 2, the position of the sensor 9 with respect to the pipe 1 is shown in three individual positions. The resultant parabolic course 12 of the pipe curvature is shown in the upper part of the figure, in which connection the trigger level 13 can be adjusted as desired within a certain bandwidth. The trigger points for the determination of the summit point 6 are marked S1 and S2 in the lower part of the figure.

Figure 3:
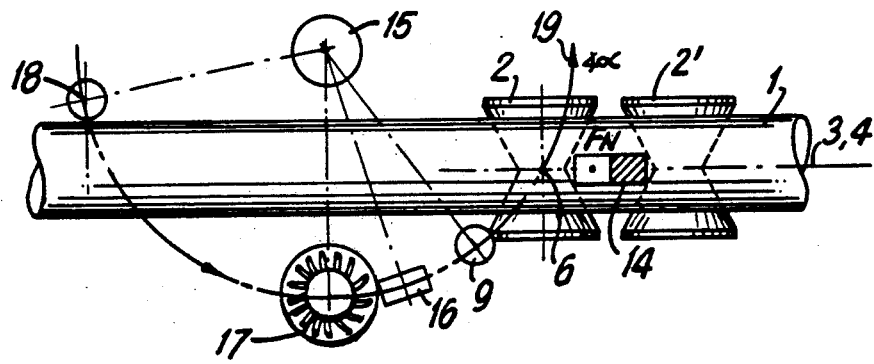
FIG. 3 shows the test station of the invention diagrammatically in a top view.
Figure 4:
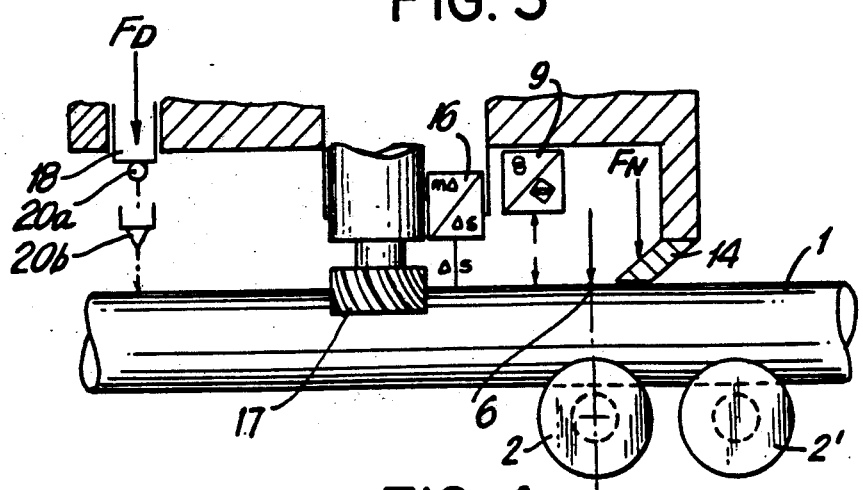
FIG. 4 is a front view of the station shown in FIG. 3.

FIG. 3 shows the test station of the invention diagrammatically in a top view and FIG. 4 shows it in a front view. The pipe 1 to be tested is pressed down by a holding-down device 14 on the rollers 2, 2' by the force $F_N$ and clamped fast. In this connection, the ideal connection is assumed, namely, that the pipe axis 3 is aligned with the machine axis 4 of the test station. At a fixed distance from the machine axis 4, the sensor 9 for the detection of the summit point or zenith 6 and, behind it, a sensor 16 for the setting of the depth of machining (see FIG. 5 and 6) as well the machining tool 17 and the penetration body 18 of the hardness testing instrument (not shown here) are arranged swingably on an axis of rotation 15. The arrow 19 designates the travel path alpha ($\alpha$) moved over upon the swinging movement. The penetration body 18 is pressed with a predetermined force $F_D$ onto the center of the previously machined area into the pipe 1. The optional use of the Brinell ball 19 or a Vickers pyramid 20 is diagrammatically indicated here.

Figure 5:
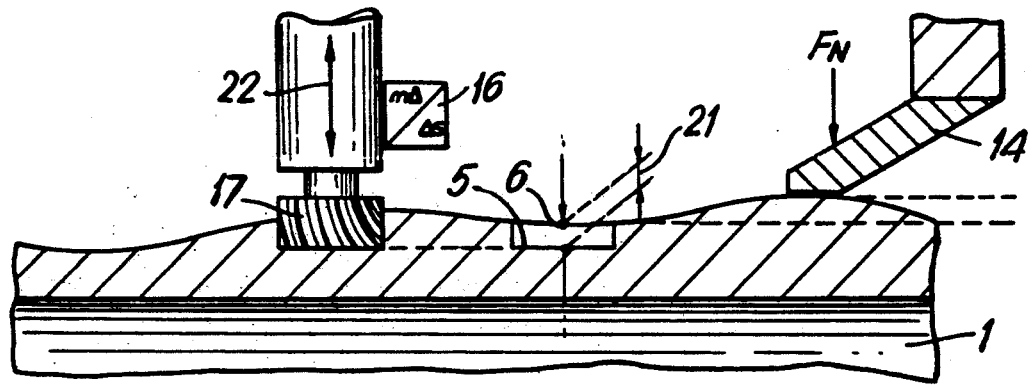
FIGS. 5 and 6 show diagrammatically the adjustment of the depth of machining in the case of pipes with very uneven surface.
Figure 6:
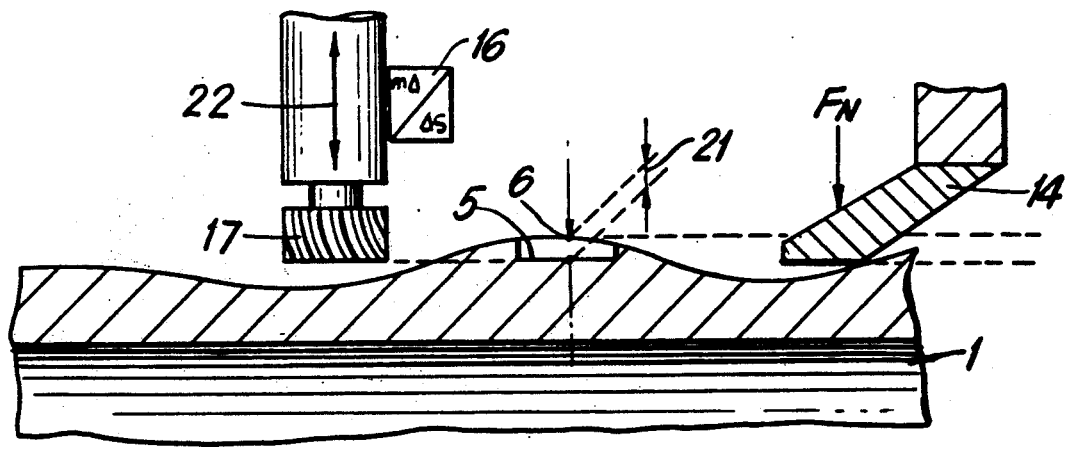

In FIGS. 5 and 6 the setting of the depth of machining 21 in the case of pipes 1 with strongly uneven surface is shown diagrammatically on basis of two examples. As a machining tool 17 for the production of the machined impression area 5 there is used in this case a milling cutter since a milled surface is entirely flat and does not tend towards barreling in the way that a ground surface does. The sensor 16 which is arranged in front of the machining tool 17 measures, at the predetermined summit point 6, the vertical position of the pipe which corresponds to the zero position of the machining tool 17. From there on, the predetermined area is machined with the predetermined desired value for the milling depth 21.

The vertical displaceability of the machining tool 17 is indicated by an arrow 22.

Figure 7:
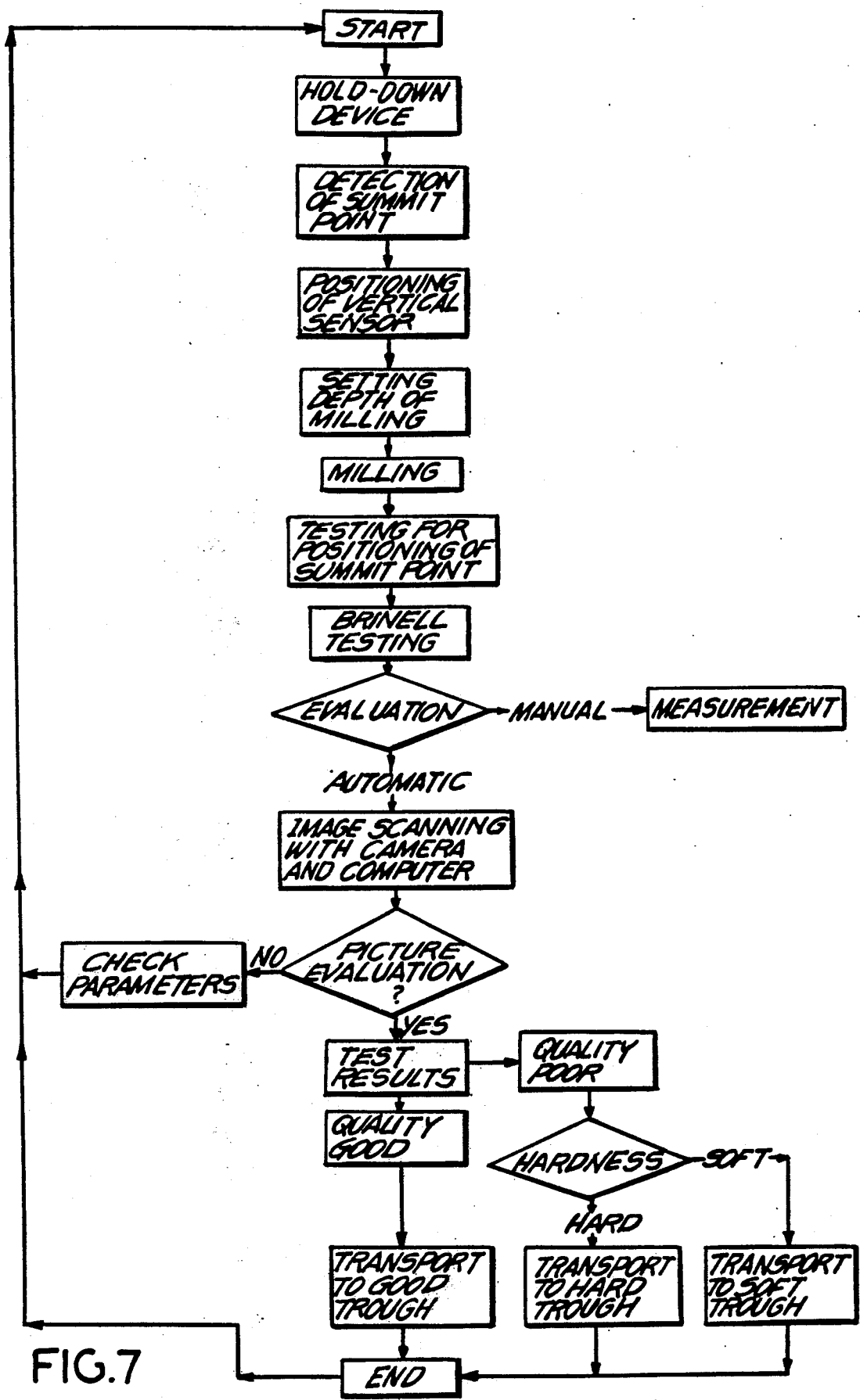
FIG. 7 is a flow chart of the process of the invention.

In FIG. 7 the flow chart of the method of the invention is shown. Depending on the result of the test, the pipes may be automatically discharged into different troughs so that the flow of material for the good pipes remains undisturbed.

Figure 8:
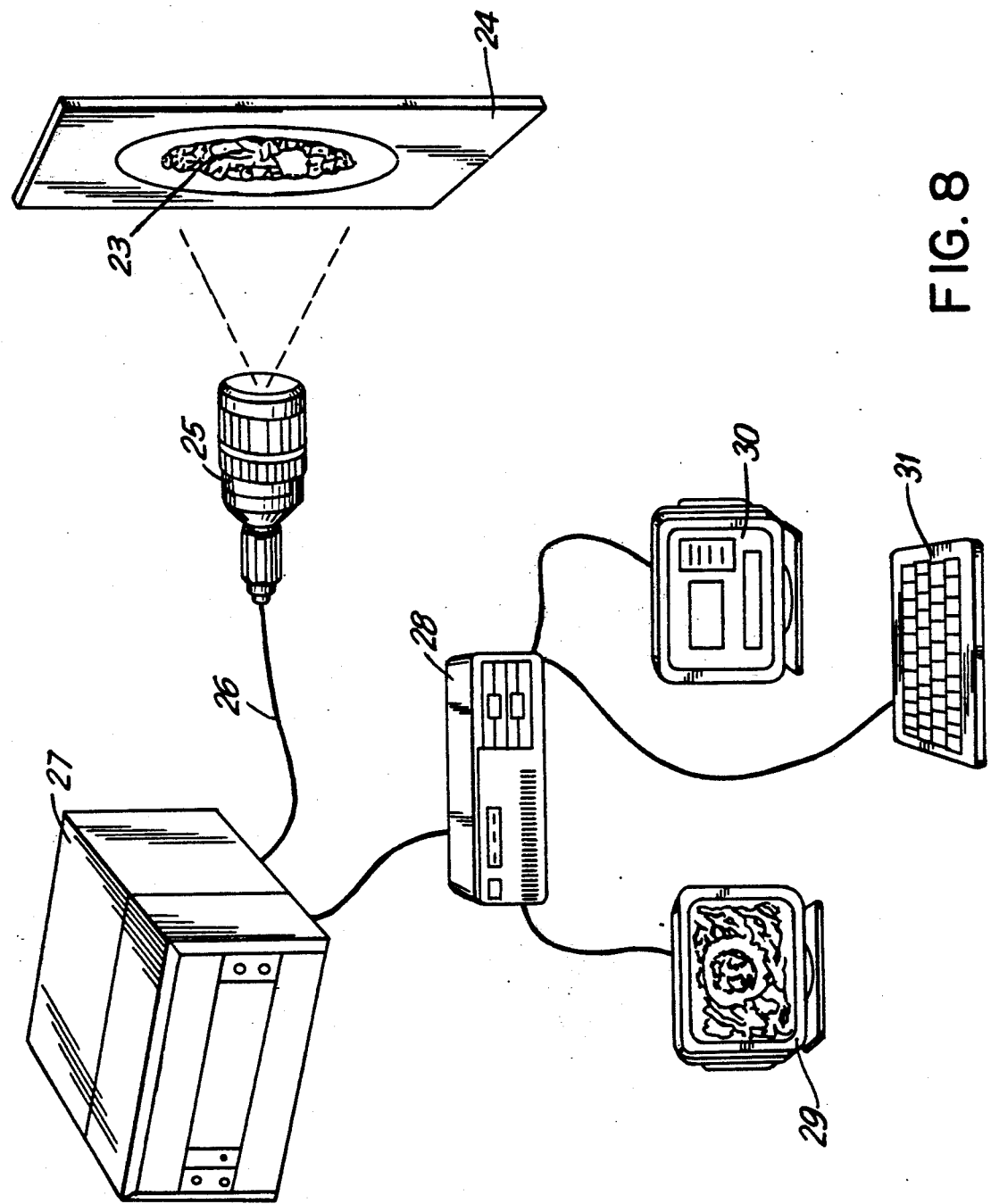
FIG. 8 shows the measurement device for the detection of the ground-glass picture.

FIG. 8 shows the measurement device for obtaining an image of the impression surface 23 on the screen or ground glass 24 in order to automate the determination of the hardness value. A diode-matrix camera 25—only the optical system has been shown here—scans the area of the image of the impression surface 23 on the ground glass 24. The camera 25 is connected by a cable 26 to an evaluation unit 27 which, in turn, is connected to a computer 28. The image of the impression surface 23 can additionally be projected onto a control monitor 29 while the surface data obtained, including the test parameters, appear on a data monitor 30. The keyboard 31 serves as control unit for the starting and ending of the test program and can, however, also be used in order to enter various questions with regard to the determination of the surfaces.

It should be understood that the preferred embodiments and examples described are for illustrative purposes only and are not to be construed as limiting the scope of the present invention which is properly delineated only in the appended claims.

We claim:

1. A method of testing the hardness of a workpiece having a continuously curved outer surface, in particular a pipe or rod, by the penetration method, comprising:
    (a) holding the workpiece in a horizontally and vertically fixed position; (b) arranging a machining tool and a hardness testing instrument having a penetration body above said workpiece for movement with respect to said workpiece; (c) linearly scanning a predetermined area of said curved surface of said workpiece for determining the distance between a distance sensor and said surface, said area lying in the horizontal path of said machining tool; (d) determining the summit point of said scanned curved surface area from said scanning operation of step (c); (e) selecting said scanned curved area as the test location for the horizontal positioning of said hardness testing instrument; (f) selecting said summit point within said scanned area of said workpiece as the reference point for the vertical positioning of said machining tool; (g) performing a second distance measurement for determining the vertical position of said summit point; (h) utilizing said position for a fine vertical position of said machine tool; (i) machining a region into the surface of said workpiece; (j) pressing said penetration body with a defined force into said machined region to generate an impression surface in said machined region of said workpiece; and (k) determining the hardness of said workpiece from said surface of said depression.

2. The method according to claim 1, wherein said workpiece is a pipe having a wall thickness and additionally comprising the step of (l) measuring the remaining wall thickness of said workpiece in said machined region without contacting said region.

3. An apparatus for testing the hardness of a workpiece having a continuously curved outer surface, the apparatus comprising means for holding the workpiece in a horizontally and vertically fixed position on a workpiece support having an axis, a machining tool for machining a region into the surface of the workpiece, and a hardness testing instrument including a penetration body for testing the hardness of the machined region, the machining tool and the hardness testing instrument being mounted on a vertically adjustable and horizontally movable holding means, the holding means being pivotal about an axis of rotation for moving the machining tool and the hardness testing instrument along an arcuate path over the workpiece, the axis of rotation being disposed at a predetermined distance from and perpendicular to the axis of the workpiece support, a first distance sensor disposed in front of the machining tool and movable horizontally along the arcuate path for linearly scanning a predetermined area of the curved surface of the workpiece and for measuring the distance between the first distance sensor and the curved surface along the scanned area, a control unit electrically connected to the first distance sensor for determining a summit point within the scanned area and providing a reference point for the vertical positioning of the machining unit, and a second distance sensor electrically connected to the control unit for determining the vertical position of the summit point, the second distance sensor being mounted on a vertical adjustment means connected to the holding means for effecting a fine vertical adjustment of the machining tool prior to machining the region.

4. The apparatus according to claim 3, wherein said workpiece to be treated has a wall thickness, the apparatus additionally comprising means at said holding means behind said machining tool for measuring said wall thickness without contacting said workpiece after machining of said workpiece.

* * * * *